United States Patent [19]

Kashmer et al.

[11] 4,061,160

[45] Dec. 6, 1977

[54] CONTROL VALVE

[75] Inventors: James S. Kashmer, Budd Lake, N.J.; Charles R. Tobin, Coopersburg, Pa.

[73] Assignee: Air Products and Chemicals, Inc., Allentown, Pa.

[21] Appl. No.: 730,906

[22] Filed: Oct. 8, 1976

[51] Int. Cl.² ............................................. F16K 11/22
[52] U.S. Cl. ................................. 137/637.2; 137/861; 128/142 R
[58] Field of Search ............................ 137/637.2, 608; 128/142 R

[56] References Cited

U.S. PATENT DOCUMENTS

| 2,970,822 | 2/1961 | Ernest | 137/608 X |
| 4,008,716 | 2/1977 | Amlong | 128/142 R |

Primary Examiner—Arnold Rosenthal
Attorney, Agent, or Firm—Russell L. Brewer; Barry Moyerman

[57] ABSTRACT

A fluid control valve being a combination of a needle valve and a gate valve disposed in a manifold sleeve having an inlet, a sensor outlet and a fluid outlet. The control valve is so constructed that the gate valve controls fluid flow through the inlet and the needle valve meters fluid flow through the outlet. Simultaneously, upon opening of the gate valve and needle valve and at all times when fluid is flowing through the control valve, fluid in the form of a reference pressure is present at the sensor outlet. Control valves according to the present invention are ideally suited for use in anesthesia machines for dispensing oxygen gas into the patient breathing circuit.

12 Claims, 1 Drawing Figure

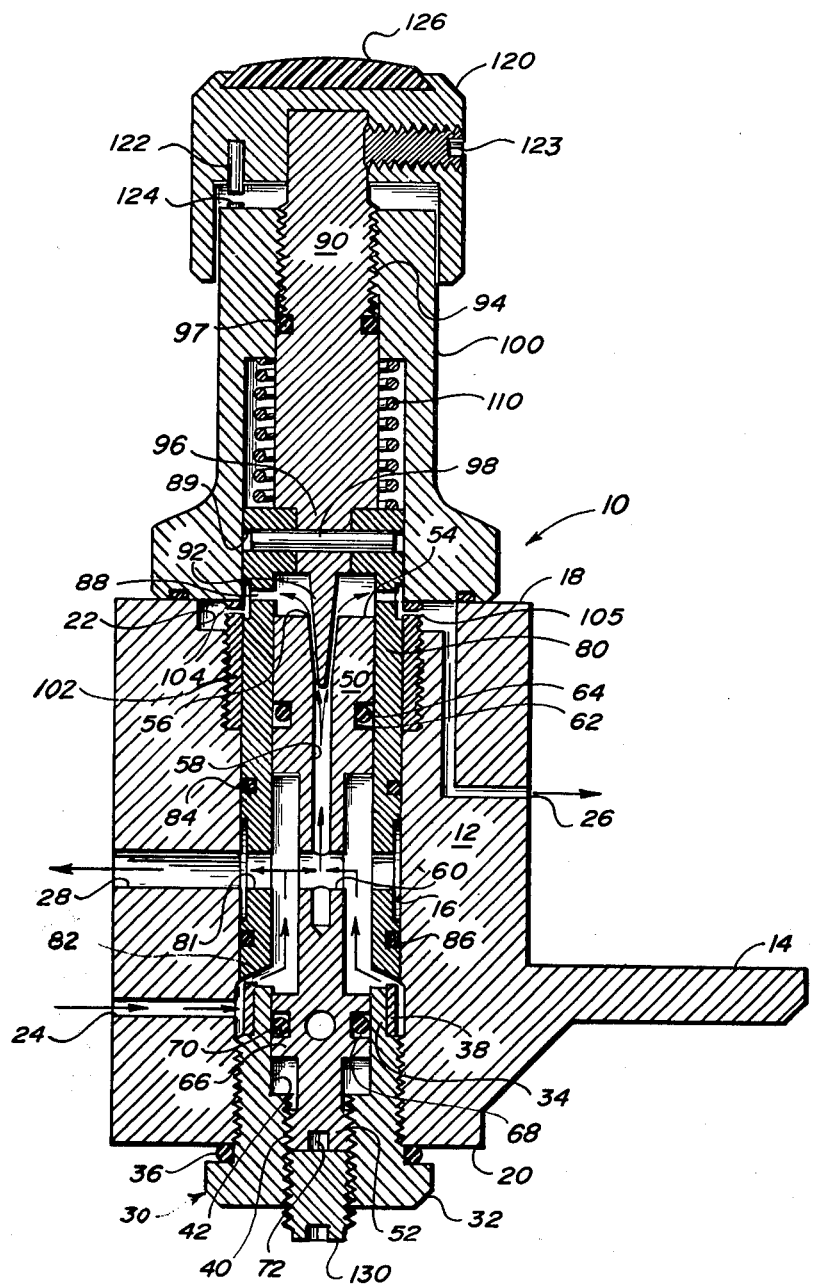

CONTROL VALVE

BACKGROUND OF THE INVENTION

1. Field of the Invention

This invention pertains to fluid control valves used to dispense a fluid wherein the valve contains means for coupling a sensor to the valve for detection and monitoring of fluid flow and fluid pressure inside the valve housing or manifold sleeve. Valves of this type are suited for use in dispensing a first or control fluid which is mixed with a second fluid or mixture of fluids. Fluid flow through or fluid pressure inside the valve housing (manifold sleeve) can be detected and used to activate the flow of the second fluid or fluids unless the first fluid is flowing at a desired pressure level through the control valve. Conversely, lack of flow or pressure inside the valve housing or manifold sleeve can be detected and used to deactivate the second control valve(s).

Valves, according to the present invention, are ideally suited for dispensing oxygen in an anesthesia machine for delivering a gas mixture of oxygen and a gaseous anesthetic agent to a patient undergoing surgery. In order to provide maximum patient safety, conventional anesthesia machines are equipped with cooperating valves so that if the oxygen flow (pressure) in the patient circuit falls below a given level, all other valves are deactivated thus stopping flow of the gaseous anesthetic agent to the patient. It is well-known that unless at least 20% of the gas mixture is oxygen, the mixture becomes highly toxic and lethal to the patient. Oxygen is required to sustain life while the patient is in a state of anesthesia.

2. Description of the Prior Art

In most conventional anesthesia machines, to provide patient safety, pressure activated check valves are provided in the anesthetic agent dispensing lines which are coupled to the oxygen delivery lines. In those systems where was no control mechanism which would relate oxygen delivered to the patient to activation or deactivation of the anesthetic agent control valves. Thus, if the anesthesiologist accidentally turned off the oxygen valve, it was possible to deliver a lethal dose of anesthetic to a patient undergoing surgery.

One solution to minimizing the risk of allowing toxic or lethal quantities of anesthetic to be delivered to a patient is shown in the article by Scurlock, published in volume 42 of *Anesthesiology*, No. 2, (February, 1975). In that reference, the author discloses the use of a fluidic device employing an OR/NOR logic gate for controlling pressure activated electric switches in an anesthesia machine. When the oxygen pressure or oxygen flow rate drops below a safe level, the pressure activated electric switches would close the anesthesia lines and an alarm would sound.

SUMMARY OF THE INVENTION

This invention relates to an improved control valve particularly adapted for use in an anesthesia machine. The improved control valve is manually operated and comprises generally a first valve controlling delivery of a fluid, c.g. oxygen, into the valve body (housing or manifold sleeve) thus providing hydraulic control pressure at a sensor outlet in the valve housing in combination with a second valve for providing metered control at a fluid outlet in the valve housing. Enhanced safety is achieved by the control valve in that hydraulic control pressure is immediately provided to the sensor outlet when there is fluid flow through the valve. The control pressure is used as a reference to activate or deactivate valves used to dispense a second fluid or fluids, e.g. anesthetic agent(s).

Therefore, it is the primary object of the present invention to provide an improved fluid control valve.

It is another object of the present invention to provide a control valve having dual functionality in that it provides hydraulic control pressure to a sensor outlet immediately after flow begins through the valve thus enabling associated valves and permits metered control of fluid flow from the valve outlet.

It is yet another object of the present invention to provide a control valve having adjustment means to provide for a pressure bleed from the sensor outlet when fluid flow is terminated at the inlet to inactivate pressure activated valves in communication with the sensor outlet.

It is still another object of the present invention to provide a control valve for use in an anesthesia machine that is simple to operate, and because of its dual functionality, provides an effective and safe means for commencing and terminating delivery of a gaseous anesthetizing mixture to a patient.

BRIEF DESCRIPTION OF THE DRAWING

The single FIGURE of the drawing is a view in cross-section of the preferred embodiment of the control valve of this invention.

DETAILED DESCRIPTION OF THE PREFERRED EMBODIMENT

The single figure of the drawing shows a control valve generally indicated by the numeral 10 which valve is ideally suited for controlling oxygen flow in a conventional anesthesia machine.

Control valve 10 includes a body or first housing 12 which hereinafter is referred to as a manifold sleeve or sleeve 12. The manifold sleeve 12 can be installed in a conventional anesthesia machine by means of flange adaptor 14 formed as an integral part of sleeve 12. Flange 14 can be provided with mounting holes or recesses (not shown) as is well-known in the art. Manifold sleeve 12 has a generally cylindrical bore 16 extending from a proximal end 18 to a distal end 20. Proximal end 18 of sleeve 12 includes a shallow counterbore recess 22 axially aligned with bore 16. A portion of bore 16 is threaded adjacent the proximal end 18 below counterbore 16 and adjacent the distal end 20 inwardly for a portion of the bore 16, the function of which will be explained hereinafter.

Sleeve 12 includes a fluid inlet passage 24 which is adapted to be connected to a source of gas (not shown) such as oxygen. A fluid outlet passage 26 extends from the bottom of counterbore recess 22 externally of the sleeve 12 and is adapted to be connected to a delivery system (not shown) for mixing delivered oxygen with an anesthetic agent for delivery to a patient via the patient circuit. Also included in sleeve 12 is a sensor passage 28 which extends from bore 16 outwardly of sleeve 12.

A hollow, generally cylindrical plug 30, having a knobbed end 32 opposite to a shouldered end 34, is disposed in the threaded portion of bore 16 of sleeve 12 adjacent end 20. Sealing between the knobbed end 32 of plug 30 is achieved by means of an O-ring 36 disposed between the sleeve 12 and plug 30. Resilient sleeve 38 made of a suitable gasket type material such as polyethylene is supported on the shouldered portion 34 of plug 30. Sleeve 38 provides a valve seat against which a valve stem can be forced to control fluid flow as will hereinafter be more fully described.

Plug 30 includes a stepped, cylindrical bore having a first threaded portion 40 and a second smooth bore portion 42.

Valve slider 50 having a threaded adjusting end 52 disposed within the threaded portion 40 of plug 30, extends longitudinally within bore 16 of sleeve 12 terminating in a hollow seat end 54. The seat end 54 contains a tapered surface 56 extending from end 54 and terminating in a generally hollow cylindrical bore 58 extending into valve slider 50 to a point below that adjacent to sensor outlet passage 28. A cross passage 60 opens the bore 58 outside of slider 50, the function of which will be hereinafter explained more fully. Seat portion 54 of slider 50 has a generally cylindrical groove 62 having disposed therein an O-ring 64. Threaded end 52 of slider 50 contains an enlarged cylindrical portion 66 having therein a cylindrical groove 68. An O-ring seal 70 is disposed within groove 68 for providing a fluid tight seal between enlarged cylindrical portion 66 of slider 50 and smooth cylindrical bore 42 of plug 30. Threaded end 52 of slider 50 includes a transverse slotted aperture 72 which is adapted to provide adjustment of the valve slider portion by means of conventional tools such as a screwdriver.

Disposed within a major portion of cylindrical bore 16 of sleeve 12 is a first generally cylindrical valve member 80 having a stepped cylindrical bore therethrough terminating at one end 82 in a tapered valve surface which is disposed in juxtaposition to resilient sleeve 38 for seating thereon. First valve member 80 contains suitable cylindrical recesses with O-rings 84, 86 disposed therein for providing a fluid tight seal between first valve member 80 and bore 16 of sleeve 16. Transverse passage 88 extends through both walls of valve 80 and is positioned in axial alignment with transverse passage 60 of valve slider 50.

A second valve member 90 having the general shape of a stepped cylinder has a tapered valve 92 projecting from its lower most cylindrical portion 96. At the end opposite tapered valve 92 the secod valve member 90 includes a threaded portion 94 and a suitable groove and O-ring 97 disposed therein. Second valve member 90 is constructed so that the lower most cylindrical portion 96 can be force fit into the upper portion of first valve 80 so that tapered valve 92 can be reciprocated in relation to and mate with the tapered surface 56 of seat end 54 of slider 50. Intimate mechanical contact between first valve 80 and second valve 90 is achieved by means of a wrist or lock pin 98 disposed in suitable transverse passages such as 89 provided in the first valve member 80 and a complementary co-axial passage provided in second valve member 90.

Disposed within the threaded portion of the bore 16 adjacent proximal end 18 of sleeve 12 is the depending threaded collar 102 of a control valve housing 100. Valve housing 100 has a generally stepped cylindrical bore therethrough, with the depending threaded collar 102 including a pair of opposite transverse passages 104–105 which are placed to provide a passage from the interior of valve housing 100 to annular passage 22 of mainfold 12. The smaller cylindrical bore portion of valve housing 100 contains a threaded portion complementary to the threaded portion of second valve member 90 so that valve members 80 and 90 can be rotated within the valve housing 100 and valve sleeve 12 to move valve surface 82 into and out of contact with resilient sleeve 38 and simultaneously valve 92 in relation to surface 56. A spring 110 is disposed within the larger cylindrical bore portion of valve housing 100 against the upper end of first valve member 80 to prevent wobble or accidental rotation of valve members 80 and 90 which ultimately will affect the flow rate of the gas passing through the valve 10.

Adjustment of the valve 10 is effected by means of a cap 120 secured to the end of second valve member 90 projecting beyond valve housing 100 by means of a set screw or other fastening device 123. Overtightening of the control valve 10 which could cause damage particularly with respect to the tapered valve 92 or its corresponding valve seat 56 is prevented by means of a peg 122 and boss 124 as is well-known in the art.

Cap 120 includes a suitable recess for indicator 126 which may be a label or medallion identifying the type of fluid which the valve controls.

Plug 30 has included a threaded locking plug 130 which serves to fix the position of valve slider 50 after it has been adjusted, as will hereinafter be more fully explained.

When the control valve 10 is assembled according to the relationship described above and shown in the drawing it is quite apparent that if cap 120 is rotated, the subassembly consisting of first valve member 80 and second valve member 90 will also rotate. If the rotation is such that first valve member 80 moves in a direction to move the tapered valve surface 82 away from resilient sleeve 38, a passage is defined that extends from fluid inlet 24 past tapered valve seat 82 through the bore of first valve member 80 through transverse passage 60 into longitudinal passage 58 of valve slider 50 into the upper portion of the cylindrical bore of first valve member 80 through transverse passage 88, through transverse passage 104 and 105 of housing 100 into counterbore recess 22 through conduit 26 outwardly of the valve 10 thus defining a complete gas passage from inlet passage 24 to outlet passage 26. Simultaneously, fluid or gas can flow from inlet 24 past the valve seat 82 into the lower cylindrical bore portion of first valve member 80 through transverse passage 81 of first valve member 80 and into sensor outlet passage 28.

It is apparent that the first valve member 80 has a valve surface 82 which seats against resilient sleeve 38 and second valve member 90 has tapered valve 92 which seats against the mating tapered outlet surface 56 of slider 50. Thus there is an inlet or gate valve defined by surface 82 and sleeve 38 and an outlet or metering (needle) valve defined by tapered valve 92 and the upper internal surface 56 of slider 50.

Having described the elements of the control valve 10, the relationship of these elements and adjustments necessary for proper control of the valve can best be explained assuming the control valve were engaged in an anesthesia machine (not shown). On engagement, fluid inlet passage 24 is connected to an oxygen supply source (not shown) and sensor outlet passage 28 is connected to a line communicating with pressure activated check valves (not shown) present in anesthesia lines in the machine. Fluid outlet passage 26 is connected to a flow meter so that the amount of oxygen passing through the metered or controlled portion of the control valve 10 of this invention can be accurately determined This output from fluid outlet 26 may be delivered to a vaporizer for entraining a vaporized anesthetic in the oxygen gas, thus forming an anesthetizing atmosphere, or it can be delivered to a patient directly.

To achieve proper operation of the control valve in an anesthesia machine, the control valve should be adjusted so that a small amount of oxygen will flow through the fluid outlet 26 for delivery to a patient so long as there is sufficient pressure at the sensor outlet 28 to activate the pressure activated valves in the anesthesia lines. In that way, a patient is assured of obtaining some oxygen, when there is sufficient pressure at the sensor outlet passage 28 to activate the check valves. By the incorporation of this feature the patient normally cannot be exposed to an atmosphere containing toxic dosages of anesthetic as might happen on shutdown or disablement of the oxygen valve of the anesthesia machine.

Proper adjustment of the control valve of this invention is achieved in the following manner. With the control valve fully assembled the combination of first valve member 80 and second valve member 90 are rotated and reciprocated inwardly as far as possible with respect to manifold sleeve 12. Further inward movement is prevented by the engagement of tapered valve surface 82 butting and sealing against resilient sleeve 38. At this point, cap 120 is placed over the end of second valve member 90 and positioned so that peg 122 butts against boss 124. Then, set screw 123 is engaged with second valve member 90. In this way overtightening of the first and second valve members (80 and 90) is prevented. Once this is done, the combination of first valve member 80 and second valve member 90 is reciprocated outward slightly with respect to manifold sleeve 12 to permit oxygen to enter fluid inlet passage 24 and pass through the interior bore of first valve member 80 out passage 81 to sensor outlet passage 28. Because of the small degree of taper in tapered valve surface 82, a hydraulic control pressure (substantially equivalent to the fluid inlet pressure) for activating pressure control valves in the anesthetic agent lines of the anesthesia machine is provided at sensor outlet passage 28. Simultaneously, with the pressurization at sensor outlet 28 oxygen passes through transverse passage 60 and bore 58 of slider 50 to the valve seat portion of slider 50. Then, the combination of first valve member 80 and second valve member 90 is moved inwardly in close fluid inlet passage 24 and then valve slider 50 is adjusted longitudinally with respect to manifold sleeve 12 to provide an output bleed of fluid in passage 26. When an appropriate bleed rate at fluid outlet passage 26 is established, valve slider 70 is locked into position by lock screw 130. Thi bleed or flow should be sufficient to permit enough oxygen to form a life supporting atmosphere anytime there is sufficient activating pressure at sensor passage 28 to activate the pressure activated check valves.

It is to be understood that further embodiments of this invention can be made without the parting from the spirit of this invention. For example, the control valve of this invention has been defined as comprising three parts, namely a manifold sleeve, valve housing and a plug. However, it is within the skill of those in the art to incorporate these components into one unit by appropriate machining with each serving their effective functions as described herein. It is also possible to alter the valve member-valve seat arrangement without detracting from the spirit of this invention, as for example, incorporating a resilient sleeve on the first valve member and a valve seat on the second valve member with the valve surface on the valve slider. All such concepts are intended to be within the definitions used for such structure herein.

Having thus described our invention, what we desire to be secured by Letters Patent of the United States is set out in the appended claims.

What is Claimed is:

1. A control valve comprising:

a manifold sleeve including a fluid inlet, a sensor outlet and a fluid outlet all of which link the interior of the manifold sleeve to the exterior thereof, said sleeve having a proximal and a distal end with the fluid inlet being located adjacent the distal end;

a hollow plug mounted in the distal end of said sleeve to seal it, the interior of said plug being in concentric alignment with the interior of said sleeve, said plug including a portion which extends longitudinally into the interior of the sleeve;

a hollow valve housing mounted on the proximal end of said sleeve to seal it, the interior of said housing being in concentric alignment with the interior of said sleeve;

a first valve member, generally tubular in cross-section, which is reciprocally and concentrically mounted within said sleeve, in juxtaposition with the interior walls thereof, said valve member terminating proximate said fluid inlet in a valve surface, said valve member also including a radial passageway proximate each of said sensor and fluid outlets;

a seating surface mounted on said longitudinally extending portion of said plug, which acts in conjunction with said valve surface and which, at one extreme of reciprocation of said first valve member, completely blocks flow through said inlet and which, at the other extreme of reciprocation, permits maximum flow;

a second valve member, mounted on said first valve member and linked thereto, for reciprocation therewith, said second member having a proximal portion extending into and mounted in said valve housing, and a distal axially extending tapered valve which terminates within the tubular portion of said first valve member;

a longitudinally extending valve slider mounted reciprocally and concentrically within said first valve member, said slider including, at one end, a seat portion which mates with the tapered valve of said second valve member to control flow rate to said fluid outlet, and a terminal portion at the other end which is retained in the hollow plug, said valve slider further including passageways linking both said fluid inlet and said sensor outlet with said seat portion;

means for reciprocating the combination if said first and second valve members with respect to said manifold sleeve, between predetermined limits; and means for reciprocally positioning the valve slider with respect to the first valve member to adjust the spacing between the tapered valve and the seat portion of said valve slider;

whereby whenever there is flow through the fluid inlet, the passageways in the valve slider providing a hydraulic control pressure at said sensor outlet and fluid to said seat portion for deliveryat adjustable flow rate to said fluid outlet.

2. The control valve of claim 1 wherein said hollow plug is removably mounted in the distal end of said manifold sleeve.

3. The control valve of claim 2 wherein said hollow plug includes a shouldered portion which extends into the interior of said sleeve and said seating surface mounted on said plug is a resilient sleeve mounted on said shouldered portion.

4. The control valve of claim 1 wherein said first valve member and second valve member are mounted for rotation with respect to said manifold sleeve.

5. The control valve of claim 4 wherein said first valve member terminates in a tapered valve surface.

6. The control valve of claim 4 wherein said hollow portions of said sleeve, plug, and valve housing are generally cylindrical.

7. The control valve of claim 6 wherein said tubular portion of said first valve member is generally cylindrical.

8. A control valve comprising in combination:
a manifold sleeve having a proximal end and a distal end and including a fluid inlet, a sensor outlet and fluid outlet therebetween all of which link the interior of the manifold sleeve to the exterior thereof;
a hollow plug closing the distal end of said sleeve to seal it, the interior of said plug being in concentric alignment with the interior of said sleeve, said plug terminating in a valve seat extending into the interior of the sleeve;
a hollow valve housing mounted on the proximal end of said sleeve to seal it, the interior of said housing being in concentric alignment with the interior of said sleeve;
a first valve member, generally tubular in cross-section, which is reciprocally and concentrically mounted within said sleeve, said valve member terminating in a valve surface proximate said fluid inlet, said valve member also including a passageway proximate each of said sensor and fluid outlets, said seating surface and said valve seat cooperatively disposed in said manifold so that at one extreme of reciprocation said first valve member completely blocks flow through said inlet and at the other extreme of reciprocation, permits maximum flow through said inlet;
a second valve member, mounted on said first valve member and linked thereto for reciprocation therewith, said second member having a proximal portion extending into and mounted in said valve housing, and a distal axially extending tapered valve which terminates within the tubular portion of said first valve member;
a longitudinally extending valve slider mounted reciprocally and concentrically within said first valve member, said slider including, at one end, a seat portion which mates with the tapered valve of said second valve member to control flow rate to said fluid outlet, and a terminal portion at the other end which is retained in the hollow plug, said valve slider further including passageways linking both said fluid inlet and said sensor outlet with said seat portion; said slider being adjustable to vary the spacing between the tapered valve and the seat portion of said slider; and
means for reciprocating the combination of said first and second valve members with respect to said manifold sleeve, between predetermined limits; and
whereby whenever there is flow through the fluid inlet, the passageways in the valve slider provide a hydraulic control pressure at said sensor outlet and fluid to said seat portion of such slider for delivery fluid outlet at a flow rate determined by the position of said tapered valve.

9. The control valve of claim 8 wherein said hollow plug is removably mounted in the distal end of said manifold sleeve.

10. The control valve of claim 9 wherein said hollow plug includes a shouldered portion which extends into the interior of said sleeve and said seating surface mounted on said plug is a resilient sleeve mounted on said shouldered portion.

11. The control valve of claim 8 wherein said first valve member and second valve member are mounted for rotation with respect to said manifold sleeve.

12. The control valve of claim 8 wherein said first valve member terminates in a tapered valve surface.

* * * * *